(12) United States Patent
McIntyre

(10) Patent No.: US 6,375,654 B1
(45) Date of Patent: Apr. 23, 2002

(54) CATHETER SYSTEM WITH WORKING PORTION RADIALLY EXPANDABLE UPON ROTATION

(75) Inventor: Jon T. McIntyre, Newton, MA (US)

(73) Assignee: CardioFocus, Inc., Norton, MA (US)

( * ) Notice: Subject to any disclaimer, the term of this patent is extended or adjusted under 35 U.S.C. 154(b) by 0 days.

(21) Appl. No.: 09/574,619

(22) Filed: May 19, 2000

(51) Int. Cl.[7] .............................................. A61B 18/18
(52) U.S. Cl. ............................ 606/41; 606/194; 606/13
(58) Field of Search ........................ 606/27–31, 41–42, 606/191, 194, 198, 13, 15

(56) References Cited

U.S. PATENT DOCUMENTS

| | | | | |
|---|---|---|---|---|
| 4,209,019 A | * | 6/1980 | Dutcher et al. .............. | 128/419 |
| 4,850,351 A | | 7/1989 | Herman et al. ........... | 128/303.1 |
| 4,878,492 A | | 11/1989 | Sinofsky et al. .......... | 128/303.1 |
| 5,246,014 A | * | 9/1993 | Williams et al. ............. | 607/122 |
| 5,400,783 A | * | 3/1995 | Pomeranz et al. ........... | 128/642 |
| 5,632,767 A | | 5/1997 | Sinofsky ....................... | 607/89 |
| 5,637,877 A | | 6/1997 | Sinofsky ................... | 250/492.1 |
| 5,643,253 A | | 7/1997 | Baxter et al. ................. | 606/17 |
| 5,851,206 A | * | 12/1998 | Guglielmi et al. ............ | 606/28 |
| 5,908,415 A | * | 6/1999 | Sinofsky ........................ | 606/7 |
| 5,908,446 A | * | 6/1999 | Imran ......................... | 607/122 |
| 5,919,187 A | * | 7/1999 | Guglielmi et al. ............ | 606/32 |
| 5,980,563 A | * | 11/1999 | Tu et al. ...................... | 607/113 |
| 5,997,571 A | | 12/1999 | Farr et al. ..................... | 607/92 |
| 6,102,908 A | * | 8/2000 | Tu et al. ........................ | 606/41 |
| 6,139,527 A | * | 8/2000 | Laufer et al. ................ | 604/114 |
| 6,228,109 B1 | * | 5/2001 | Tu et al. ...................... | 607/113 |
| 6,267,781 B1 | * | 7/2001 | Tu ............................... | 607/113 |
| 6,280,441 B1 | * | 8/2001 | Ryan ............................. | 606/45 |

OTHER PUBLICATIONS

Keane, D. et al., "Linear Atrial Ablation with a Diode Laser and Fiberoptic Catheter," *Circulation*, p. 1–2, Oct. 5, 1999.

Ware, D.L., "Slow Intramural Heating with Diffused Laser Light: A Unique Method for Deep Myocardial Coagulation," *Circulation*, pp. 1630–1636, Mar. 30, 1999.

* cited by examiner

*Primary Examiner*—Michael Peffley
(74) *Attorney, Agent, or Firm*—Hamilton Brook Smith & Reynolds, P.C.

(57) ABSTRACT

A catheter system is formed of a two-lumen rotatable shaft with a working tube extending through one of the lumens and an energy emitting element coupled to the other lumen. Rotation and movement distally of the rotatable shaft, coils the energy emitting element and expands the overall profile of the catheter system. Energy emitted through the coiled energy emitting element provides circular lesions for circumferential treatment on desired tissue. Counter rotating and retracting of the rotatable shaft returns the catheter system to a sleek profile for removal of the catheter system from the biological vessel area. A light diffusing tip with reflective sheath is utilized as the energy emitting element and focuses energy on the target tissue and away from surrounding blood pool.

27 Claims, 2 Drawing Sheets

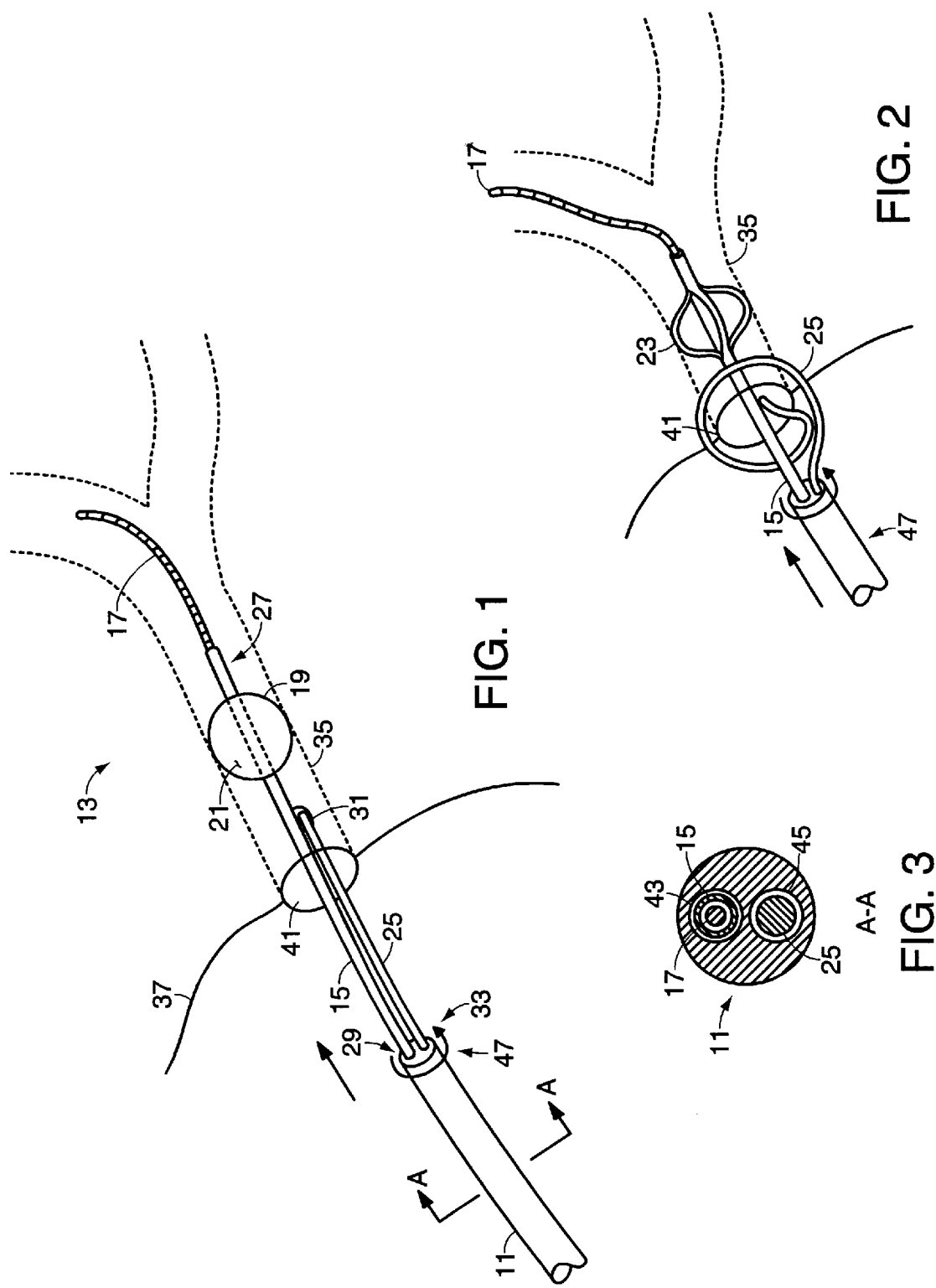

CATHETER SYSTEM WITH WORKING PORTION RADIALLY EXPANDABLE UPON ROTATION

BACKGROUND OF THE INVENTION

A variety of energy sources have been utilized to create therapeutic lesions in the human body. These energy sources include radio frequency, ultrasound, microwave and cryo. Recently it has also been demonstrated that diode laser energy can be used for these purposes.

Cardiac tissue is often the target of such energy applications for the treatment of various arrhythmias (abnormal rhythms of the heart). One such arrhythmia is atrial fibrillation. In treating atrial fibrillation, lesions in the walls of the heart are created to subsequently produce scar tissue. The scar tissue blocks errant "electrical" signals from propagating through the atrium or redirects the signals to the A-V node so as to restore the normal rhythm.

Traditionally the use of lasers in medicine has been through devices that deliver a single, narrow beam of light forward to vaporize (destroy) tissue. In cardiology applications such as atrial fibrillation, this has given rise to the concern for the potential risk of tissue perforation by the beam of light. Sinofsky in U.S. Pat. Nos. 5,908,415 5,643,253 and 4,878,492 disclosed devices and methods for the controlled and uniform delivery of light (photonic) energy to target tissue. This type of delivery also eliminates the risk of wall perforation by a beam of light.

The primary mechanism by which photonic energy functions is rapid and volumetric absorption by the tissue to cause coagulative necrosis. It does not rely on conductive heating from a burst of energy that occurs at the interface of the device and tissue. Peak temperature and absorption is below the tissue surface, avoiding tissue disruption at the catheter tissue interface. This clean formation of the lesion can avoid surface issues such as carbonization and clot formation. Appropriate use of parameters such as power and time help in the avoidance of these complications.

Another concern is that current ablation procedures for atrial fibrillation can be lengthy to perform. This is due largely to the limitations of current technologies in efficiently producing complete lines of conduction block without several tedious applications of energy. The use of laser devices propose the ability to quickly create a long transmural lesion (less than two minutes) with far fewer applications of energy. Thus the required ablating time is potentially greatly reduced.

It has been learned recently that circumferential lesions in the areas of the pulmonary veins located in the left atrium may be useful in the treatment of atrial fibrillation. The most common approach (percutaneously) to the left atrium involves creating a path from the right atrium through the atrial septum, commonly referred to as a "septal puncture". Some of the challenges related to this approach and treatment include passing a relatively small diameter (2.67–4.67 mm) device through the septal puncture that is still able to create a relatively large (15–30 mm diameter) circular lesion. Another challenge stems from a potential complication of delivering energy inside the pulmonary vein known as "pulmonary vein stenosis".

SUMMARY OF THE INVENTION

The present invention provides a catheter system for overcoming the shortcomings of the prior art and in particular addressing the foregoing issues in circumferential lesions for the treatment of atrial fibrillation.

The invention catheter system includes:

a rotatable shaft having two lumens, the rotatable shaft being rotatable about a longitudinal axis and having a distal end and a proximal end;

working tube passing freely in one lumen of the rotatable shaft, the working tube having a length with a proximal end and a distal end disposed outside the distal end of the rotatable shaft;

and an energy emitting element having one end fixed into the other lumen of the rotatable shaft and an opposite end extending from the distal end of the rotatable shaft and coupled to the working tube between the proximal end and distal end of the working tube, wherein upon rotation of the rotatable shaft the energy emitting element forms coils around the working tube and upon movement of the rotatable shaft toward the distal end of the working tube, the coils of the energy emitting element become larger in circumference such that a radially expandable portion of the catheter system is defined.

In the preferred embodiment the working tube has (1) a longitudinal area along its length for passage of a movable guide wire to position the catheter system in a biological vessel, and (2) centering means coupled to its distal end, for coaxially centering the working tube in the biological vessel. The centering means may include an elastomeric balloon or radially expanding arms or other suitable elements for centering the working tube in the vessel.

Also in the preferred embodiment the opposite end of the energy emitting element is coupled to the working tube adjacent the centering means, and the rotatable shaft is simultaneously rotated and moved distally (i.e., toward the distal end of the working tube). Further the coils of the energy emitting element that define the radially expandable portion of the catheter system preferably make contact with the walls outside of the biological vessel orifice. As such, desired circumferential (circular) lesions are created. Alternatively, the coiled energy emitting element makes contact with biological tissue inside a vessel and produces desired circumferential lesions.

The energy emitting element may emit radio frequency, microwave, cryo or ultrasound energy.

In another embodiment, the energy emitting element is slidably disposed in a coilable tube.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 is a schematic diagram of a catheter system of the present invention as used in a pulmonary vein at the left atrial wall.

FIG. 2 is a schematic illustration of the catheter system of FIG. 1 in a rotated, expanded and centered mode of operation.

FIG. 3 is a cross section through line A—A of FIG. 1.

DETAILED DESCRIPTION OF THE INVENTION

Figure 4:
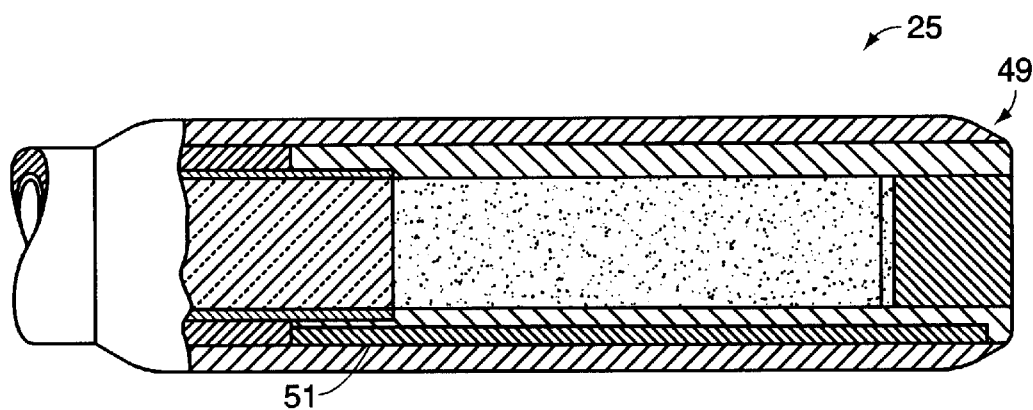
FIG. 4 is a sectional view of a light diffusing tip with reflector employed in the embodiment of FIG. 1.

As illustrated in FIG. 1, the invention catheter system 13 is formed of a rotatable shaft 11, working tube 15 and energy emitting element 25. The rotatable shaft 11 is a two-lumen shaft having lumens 43 and 45 illustrated in FIG. 3. The working tube 15 passes freely throughout the lumen 43 of the rotating shaft 11. The working tube 15 has a longitudinal area along its longitudinal axis which allows for passage of a commercially available movable and torqueable guide wire 17 (discussed further later). The working tube 15 has a length that exits through the distal end 47 of the rotatable shaft 11. The illustrated length of working tube 15 has a distal end 27 and proximal end 29 with respect to the working shaft 11.

As illustrated in FIG. 3 the movable guide wire 17 lies coaxially within working tube 15 which passes freely in lumen 43. The movable guide wire is formed of stainless steel or nitinol and has a diameter if ≦0.038". The working tube is formed of a polymeric material such as Pebax, polyethylene or polyurethane. Inner diameter in range of 0.032" to 0.045" with a wall thickness between 0.003" and 0.010".

At the distal end 27 of the working tube there is an element or means 19 for centering the working tube in a biological vessel when the catheter system is in use. The centering means may be an elastomeric balloon 21, or radially expanding arms 23 (such as that described in U.S. Pat. No. 5,997,571), or the like. In the case of an elastomeric balloon 21 there is a separate inflation lumen in working tube 15.

The case of radially expanding arms 23 is illustrated in FIG. 2. Two coaxially aligned tubes are disposed such that when axially moved relative to each other, a multiplicity (e.g., three or more) of arms expand radially to a vessel wall.

Returning to FIG. 1, the energy emitting element 25 has a proximal end 33 fixed to the second lumen 45 of the rotating shaft 11. The distal end 31 of the energy emitting element 25 is preferably fixed to the working tube 15 adjacent the centering means 19 (or between the distal end 27 and proximal end 29 of the working tube 15). Transitional material can be added at attachment points 31 and 33 in order to provide mechanical stress relief when the energy emitting element is in its radially expanded state shown in FIG. 2. The energy emitting element 25 has an outer diameter of about 480 to 1480 microns, preferably between 960 and 1100 microns and a length of about 4.5 cm–9.0 cm extending from the working tube distal end 27.

In the preferred embodiment, the energy emitting element 25 is a diffusing tip such as that described in U.S. Pat. No. 5,908,415 and illustrated herein in FIG. 4. The illustrated light diffusing tip utilizes a reflector 51 placed on one side of the diffusing tip 49 (about 180 degrees radially or extending around about half of the circumference, throughout the length of the energy emitting element, other circumferential reflector angles may be used). The reflector 51 is preferably formed of gold foil or other material of high reflectance and relatively low hardness such that it is easily formed into shape. The reflector 51 blocks and reflects light back towards the core area of the light diffusing tip 49. As such, the energy emitting element 25 with such a reflector 51 causes more energy to be directed toward the tissue of interest and, in the example of creating cardiac lesions, prevents light energy from being directed toward the surrounding blood pool.

Use of the catheter system 13 is then as illustrated in FIGS. 1 and 2 as follows. As shown in FIG. 1, movable guide wire 17 is positioned into a desired vessel such as the pulmonary vein 35. The guide wire 17 is inserted into working tube 15 such that the working tube 15 and hence catheter system 13 is advanced over the guide wire 17 to the desired depth within the pulmonary vein 35. The centering means 19 is then activated to engage the vein (or vessel) walls and center the working tube 15 coaxially within the pulmonary vein 35. FIG. 1 illustrates the balloon 21 method of centering working tube 15 within a pulmonary vein 35, whereas FIG. 2 illustrates the radially expanded arms 23 embodiment centering working tube 15 within a pulmonary vein 35.

Figure 5:
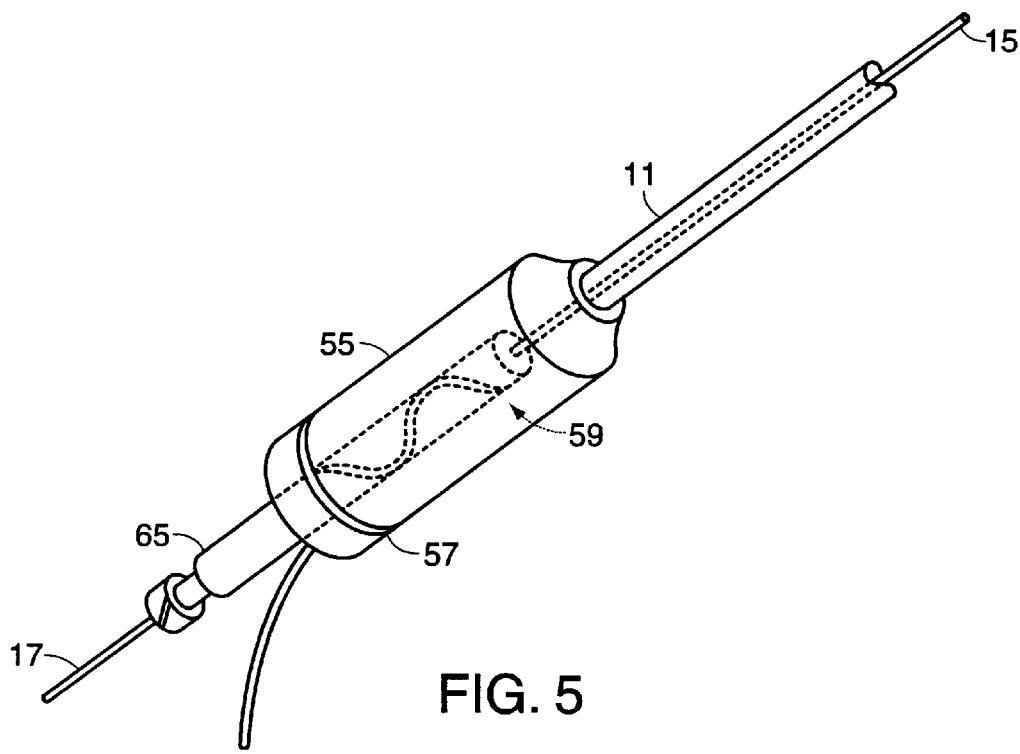
FIG. 5 is a schematic illustration of the handle of the catheter system of FIG. 1.
Figure 6:
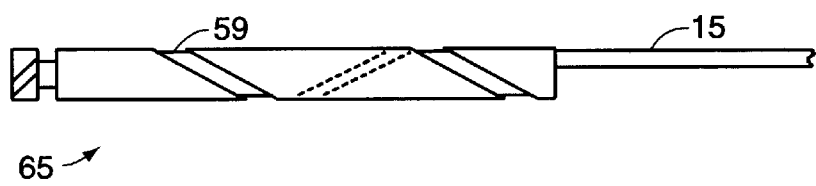
FIG. 6 is a schematic illustration of the inner handle details of the FIG. 5 handle.

The rotatable shaft 11 is then rotated and advanced forward (toward the distal end 27 of working tube 15) as illustrated in FIG. 2. This causes the energy emitting element 25 to wind around (coil about) the working tube 15 and expand radially. In particular, this rotating and movement distally of the rotating shaft 11 is performed simultaneously such that the energy emitting element 25 forms a coil around the vessel orifice 41 against abutting tissue. This simultaneous forward and rotational motion can be achieved with the handle assembly shown in FIG. 5. When the outer handle is advanced by pushing on the push washer is caused to rotate about the inner handle by a key that rides within a spiral groove of the inner handle. The working tube is fixed to the inner handle and the two lumen shaft is fixed to the outer handle. The rotation and linear travel are regulated by the helical groove. The push washer is rotationally free of the inner handle and the outer handle. When coiled and advanced distally as shown in FIG. 2, the energy emitting element 25 forms coils with a diameter of about 20 mm or greater. Typical pulmonary vein inner diameters are about 15 mm to 25 mm and thus the coiled energy emitting element 25 generally makes contact with the tissue forming the orifice of the pulmonary vein 35 as illustrated in FIG. 2.

Energy is then applied through the energy emitting element 25 which creates the desired therapeutic lesion in a circumferential (circular) fashion outside of the subject vessel/pulmonary vein 35.

After application of the energy, the rotatable shaft 11 may be counter rotated and pulled back relative to the distal end 27 of the working tube 15. This causes the energy emitting element 25 to straighten and lie along a longitudinal axis substantially parallel with the longitudinal axis of the working tube 15, and effectively return to the starting position illustrated in FIG. 1. After the centering means 19 have been collapsed, the catheter system 13 may be safely retracted through a small area (relative to the pulmonary vein) such as through the septal puncture in the case of percutaneous treatment of atrial fibrillation.

As described herein, the present invention meets the need of creating circumferential lesions around the outside of vessels such as the pulmonary vein and coronary sinus. The disclosed catheter system overcomes the challenges of returning to a small profile device after energy application and preventing delivery of energy inside the vessel itself.

While this invention has been particularly shown and described with references to preferred embodiments thereof, it will be understood by those skilled in the art that various changes in form and details may be made therein without departing from the scope of the invention encompassed by the appended claims.

For example, the energy emitting element 25 may be slidably disposed in a tubelike housing which is coilable in the manner described above. The coilable tube/housing has a proximal end 33 secured to the second lumen 45 of rotating shaft 11 and a distal end 31 fixed to the working tube 15. The coilable tube/housing is formed of, for example, natural Pebax or other colorless polymeric material, and has inner and outer diameters of about 490–1490 microns and about 1000–3000 microns, respectively. The energy emitting element is dimensioned so as to allow slidable disposition within the coilable tube/housing. As such the coilable tube/housing serves as a conduit for the energy emitting element. The depth at which the energy emitting element is inserted into the distal end of the coilable tube/housing is indicated by radio paint markers (viewable in fluoroscopic conditions) at the distal end of the conduit and/or by indexes at the proximal end of the conduit. Various depths of insertion result in various length arcs of emitted energy and hence arc-shaped lesions (instead of full circumference lesions). A series of arc-shaped lesions may be produced and connected end-to-end to ultimately result in a full circumference overall lesion.

What is claimed is:

1. A catheter system comprising:
    a shaft having one or more lumens, the shaft having a distal end and a proximal end;
    a working tube passing freely in one lumen of the shaft, the working tube having a length, with a proximal end and a distal end, exposed outside the distal end of the shaft, the shaft and the working tube being rotatable relative to each other about a longitudinal axis; and
    an energy emitting element having one end fixed into a lumen of the shaft and an opposite end extending from the distal end of the shaft and coupled to the working tube between the proximal end and distal end of the working tube,
    wherein upon rotation of the shaft relative to the working tube, the energy emitting element forms a curve shape around the working tube and upon relative movement of the shaft toward the distal end of the working tube, the curve shape of the energy emitting element becomes radially larger such that a radially expandable portion of the catheter system is defined.

2. A catheter system as claimed in claim 1 wherein the working tube has a longitudinal area along its length for passage of a movable guide wire.

3. A catheter system as claimed in claim 1 further comprising centering means coupled to the distal end of the working tube for coaxially centering the working tube in a biological vessel.

4. A catheter system as claimed in claim 3 wherein the centering means includes an elastomeric balloon.

5. A catheter system as claimed in claim 3 wherein the centering means includes radially expanding arms.

6. A catheter system as claimed in claim 3 wherein the opposite end of the energy emitting element is coupled to the working tube adjacent the centering means.

7. A catheter system as claimed in claim 1 wherein the radially expandable portion makes contact with biological tissue outside of, but adjacent to a vessel orifice and produces desired circumferential lesions.

8. A catheter system as claimed in claim 1 wherein the radially expandable portion makes contact with biological tissue inside a vessel and produces desired circumferential lesions.

9. A catheter system as claimed in claim 1 wherein half of the energy emitted by the energy emitting element is blocked by a reflector disposed throughout its length.

10. A catheter system as claimed in claim 9 wherein the reflector is formed of gold foil.

11. A catheter system as claimed in claim 1 wherein the energy emitting element emits radio frequency energy.

12. A catheter system as claimed in claim 1 wherein the energy emitting element emits microwave energy.

13. A catheter system as claimed in claim 1 wherein the energy emitting element emits cryo energy.

14. A catheter system as claimed in claim 1 wherein the energy emitting element emits ultrasound energy.

15. A catheter system as claimed in claim 1 further comprising a handle coupled to the proximal end of the shaft in a manner for effecting rotation and distal movement of the shaft and the working tube relative to each other.

16. Catheter apparatus comprising:
    a rotatable shaft having a proximal end and a distal end, the rotatable shaft being rotatable about a longitudinal axis; and
    a coilable member having a proximal end and a distal end, the coilable member proximal end being coupled to the rotatable shaft, the coilable member emitting energy and being selectably coilable as a function of rotation of the rotatable shaft, such that upon rotation of the rotatable shaft, the coilable member forms a coil emitting energy that produces circumferential lesions on biological tissue in contact with the coil.

17. Apparatus as claimed in claim 16 wherein the rotatable shaft has two lumens and the coilable member is connected to one of the lumens.

18. Apparatus as claimed in claim 17 further comprising a working tube passing freely in the other lumen of the rotatable shaft, the working tube having a length, with a proximal end and a distal end, exposed outside the distal end of the rotatable shaft; and
    the coilable member forms the coil around the working tube.

19. Apparatus as claimed in claim 18 wherein the working tube has a longitudinal area along its length for passage of a movable guide wire.

20. Apparatus as claimed in claim 18 further comprising centering means coupled to the distal end of the working tube for coaxially centering the working tube in a biological vessel.

21. Apparatus as claimed in claim 20 wherein the distal end of the coilable member is coupled to the working tube adjacent the centering means.

22. Apparatus as claimed in claim 16 wherein the coilable member includes a coilable tube; and
    an energy emitting element slidably disposed in thy coilable tube.

23. Apparatus as claimed in claim 22 wherein half of the energy emitted by the energy emitting element is blocked by a reflector disposed throughout its length.

24. Apparatus as claimed in claim 22 wherein the energy emitting element is disposed partially in the distal end of the coilable tube, such that the coilable member produces arc-shaped lesions on biological tissue in contact with the coil.

25. Apparatus as claimed in claim 16 wherein simultaneous with rotation of the rotatable shaft, the rotatable shaft is moved distally such that the coil becomes larger in circumference.

26. Apparatus as claimed in claim 25 further comprising a handle coupled to the proximal end of the rotatable shaft in a manner for effecting rotation and distal movement of the rotatable shaft.

27. A catheter system as claimed in claim 1 wherein the energy emitting element emits photonic energy.

* * * * *